United States Patent
Andrejuk et al.

(10) Patent No.: US 11,852,621 B2
(45) Date of Patent: Dec. 26, 2023

(54) SYSTEM AND METHOD FOR MONITORING TILLED FLOOR CONDITIONS USING A TILLED FLOOR SENSING ASSEMBLY

(71) Applicant: CNH Industrial Canada, Ltd., Saskatoon (CA)

(72) Inventors: Nicholas Nahuel Andrejuk, Normal, IL (US); James W. Henry, Saskatoon (CA)

(73) Assignee: CNH Industrial Canada, Ltd., Saskatoon (CA)

( * ) Notice: Subject to any disclaimer, the term of this patent is extended or adjusted under 35 U.S.C. 154(b) by 253 days.

(21) Appl. No.: 17/211,997

(22) Filed: Mar. 25, 2021

(65) Prior Publication Data
US 2021/0333259 A1 Oct. 28, 2021

Related U.S. Application Data

(60) Provisional application No. 63/014,280, filed on Apr. 23, 2020.

(51) Int. Cl.
*G01N 33/24* (2006.01)
*B64C 25/32* (2006.01)
(Continued)

(52) U.S. Cl.
CPC .............. *G01N 33/24* (2013.01); *B64C 25/32* (2013.01); *B64C 39/024* (2013.01); *G01N 19/00* (2013.01);
(Continued)

(58) Field of Classification Search
CPC .. A01B 79/005; B64C 39/024; G05D 1/0094; G05D 1/101; H04W 4/026; B64U 2101/00
(Continued)

(56) References Cited

U.S. PATENT DOCUMENTS 4,186,878 A 2/1980 Lestradet
6,202,013 B1 3/2001 Anderson et al.
(Continued)

FOREIGN PATENT DOCUMENTS

CN 104330279 A 2/2015
CN 108152071 A 2/2015
(Continued)

OTHER PUBLICATIONS

Extended European Search Report issued in Corresponding Application No. 21169596.0-1004 dated Sep. 24, 2021 (5 pages).
(Continued)

*Primary Examiner* — Nathaniel T Woodward
(74) *Attorney, Agent, or Firm* — Rebecca Henkel; Rickard DeMille (57) ABSTRACT

A system for monitoring tilled floor conditions within a field includes a sensor frame and a tilled floor sensing assembly supported on the sensor frame. The assembly, in turn, includes a plurality of pins configured to be extended relative to the sensor frame such that each pin penetrates a top surface of the field. Furthermore, the assembly includes a plurality of position sensors, with each position sensor configured to capture data indicative of a position of a given pin of the plurality of pins relative to the sensor frame. Moreover, the assembly includes a plurality of force sensors, with each force sensor configured to capture data indicative of a force being applied to a given pin of the plurality of pins. Additionally, the data captured by the plurality of position sensors and the data captured by the plurality of force sensors is indicative of a tilled floor profile of the field.

19 Claims, 4 Drawing Sheets

(51) Int. Cl.
B64C 39/02 (2023.01)
G01N 19/00 (2006.01)
B64U 101/00 (2023.01)

(52) U.S. Cl.
CPC .... *B64U 2101/00* (2023.01); *G01N 2033/245* (2013.01)

(58) Field of Classification Search
USPC .......................................................... 701/3
See application file for complete search history.

(56) References Cited

U.S. PATENT DOCUMENTS

| | | | |
|---|---|---|---|
| 6,454,294 | B1 | 9/2002 | Bittner et al. |
| 7,752,779 | B2 | 7/2010 | Schoenmaker et al. |
| 9,382,003 | B2 | 7/2016 | Burema et al. |
| 9,994,307 | B2 | 6/2018 | Nguyen et al. |
| 10,095,235 | B2 | 10/2018 | Sugumaran et al. |
| 10,244,747 | B2 | 4/2019 | Leeb et al. |
| 10,252,285 | B2 | 4/2019 | Barker et al. |
| 11,470,763 | B2 * | 10/2022 | Barrick ................ A01B 79/005 |
| 11,483,960 | B2 * | 11/2022 | Andrejuk ................ H04W 4/38 |
| 2013/0068892 | A1 | 3/2013 | Bin Desa et al. |
| 2016/0255769 | A1 | 9/2016 | Leeb |
| 2017/0131718 | A1 | 5/2017 | Matsumura et al. |
| 2017/0305537 | A1 | 10/2017 | Smith et al. |
| 2018/0156770 | A1 * | 6/2018 | Saez ................ B64C 39/024 |
| 2018/0292339 | A1 * | 10/2018 | Gunzenhauser ..... G01N 27/045 |
| 2018/0364157 | A1 | 12/2018 | Ghiraldi et al. |
| 2020/0255139 | A1 | 8/2020 | Nahuel-Andrejuk et al. |
| 2020/0255140 | A1 | 8/2020 | Nahuel-Andrejuk et al. |
| 2020/0257318 | A1 | 8/2020 | Nahuel-Andrejuk et al. |
| 2021/0089027 | A1 * | 3/2021 | Dasika ................ G06F 3/04845 |
| 2021/0333259 | A1 * | 10/2021 | Andrejuk ............... G01N 33/24 |

FOREIGN PATENT DOCUMENTS

| | | |
|---|---|---|
| CN | 204236769 | 4/2015 |
| CN | 107235146 | 10/2017 |
| CN | 107235146 A | 10/2017 |
| CN | 107907365 A | 4/2018 |
| CN | 107963214 A | 4/2018 |
| DE | 10261138 | 6/2004 |
| EP | 3235380 | 10/2017 |
| EP | 3372078 | 9/2018 |
| GB | 2457388 | 8/2009 |
| GB | 2521343 | 5/2018 |
| KR | 2017/0014172 | 2/2017 |
| WO | WO 2016/123466 | 8/2016 |

OTHER PUBLICATIONS

Thomas-Murphy, Jenn, "Mobile Applications", Field Crops, Cornell CALS, dated 2021, (4 Pages) https://fieldcrops.cals.cornell.edu/tools-resources/mobile-apps/.

"SenseFly", Agriculture, Parrot Group, Apr. 5, 2019, (11 pages) https://www.sensefly.com/industry/agriculture/.

* cited by examiner

SYSTEM AND METHOD FOR MONITORING TILLED FLOOR CONDITIONS USING A TILLED FLOOR SENSING ASSEMBLY

CROSS-REFERENCE TO RELATED APPLICATIONS

This application is based upon and claims the right of priority to U.S. Provisional Patent Application No. 63/014,280, filed on Apr. 23, 2020, the disclosure of which is hereby incorporated by reference herein in its entirety for all purposes.

FIELD OF THE INVENTION

The present disclosure generally relates to systems and methods for monitoring tilled floor conditions within a field and, more particularly, to systems and methods for monitoring tilled floor conditions within a field using a tilled floor sensing assembly installed on a sensor frame, such as an unmanned aerial vehicle (UAV) or a hand-held device.

BACKGROUND OF THE INVENTION

Agricultural implements, such as planters, seeders, tillage implements, and/or the like, are typically configured to perform an agricultural operation within a field, such as a planting/seeding operation, a tillage operation, and/or the like. When performing such agricultural operations, it is desirable to adjust the operation of the implement to account for variations in the tilled floor profile of the field that could potentially impact the effectiveness and/or efficiency of the operation. In this regard, systems have been developed that allow the profile of the tilled floor of the field to be determined as the implement is traveling across the field. However, further improvements to such systems are needed.

Accordingly, an improved system and method for monitoring tilled floor conditions within a field would be welcomed in the technology.

SUMMARY OF THE INVENTION

Aspects and advantages of the technology will be set forth in part in the following description, or may be obvious from the description, or may be learned through practice of the technology.

In one aspect, the present subject matter is directed to a system for monitoring tilled floor conditions within a field. The system includes a sensor frame and a tilled floor sensing assembly supported on the sensor frame. The tilled floor sensing assembly, in turn, includes a plurality of pins configured to be extended relative to the sensor frame such that each pin penetrates a top surface of the field. Furthermore, the tilled floor sensing assembly includes a plurality of position sensors, with each position sensor configured to capture data indicative of a position of a given pin of the plurality of pins relative to the sensor frame. Moreover, the tilled floor sensing assembly includes a plurality of force sensors, with each force sensor configured to capture data indicative of a force being applied to a given pin of the plurality of pins. In this respect, the data captured by the plurality of position sensors and the data captured by the plurality of force sensors is indicative of a tilled floor profile of the field.

In another aspect, the present subject matter is directed to a method for monitoring tilled floor conditions within a field. The method includes initiating, with a computing system, extension of a plurality of pins relative to the sensor frame such that each pin penetrates a top surface of the field. Furthermore, the method includes receiving, with the computing system, position sensor data indicative of a position of each pin of the plurality of pins relative to the sensor frame. Additionally, the method includes receiving, with the computing system, force sensor data indicative a force being applied to each pin of the plurality of pins. Moreover, the method includes determining, with the computing system, a tilled floor profile of the field based on the received position sensor data and the received force sensor data.

These and other features, aspects and advantages of the present technology will become better understood with reference to the following description and appended claims. The accompanying drawings, which are incorporated in and constitute a part of this specification, illustrate embodiments of the technology and, together with the description, serve to explain the principles of the technology.

BRIEF DESCRIPTION OF THE DRAWINGS

A full and enabling disclosure of the present technology, including the best mode thereof, directed to one of ordinary skill in the art, is set forth in the specification, which makes reference to the appended figures, in which.

Repeat use of reference characters in the present specification and drawings is intended to represent the same or analogous features or elements of the present technology.

DETAILED DESCRIPTION OF THE DRAWINGS

Reference now will be made in detail to embodiments of the invention, one or more examples of which are illustrated in the drawings. Each example is provided by way of explanation of the invention, not limitation of the invention. In fact, it will be apparent to those skilled in the art that various modifications and variations can be made in the present invention without departing from the scope or spirit of the invention. For instance, features illustrated or described as part of one embodiment can be used with another embodiment to yield a still further embodiment. Thus, it is intended that the present invention covers such modifications and variations as come within the scope of the appended claims and their equivalents.

In general, the present subject matter is directed to systems and methods for monitoring tilled floor conditions within a field. Specifically, in several embodiments, the system may include a sensor frame and a tilled floor sensing assembly supported on the sensor frame. In one embodiment, the sensor frame may be configured as an unmanned aerial vehicle (UAV). In such an embodiment, the tilled floor sensing assembly may be configured to capture data indicative of the profile of the tilled floor of the field when the sensor frame lands at a data collection point. In another embodiment, the sensor frame may be a hand-held device having handles that permit the operator to move the sensor frame relative to field. In such an embodiment, the operator may carry the sensor frame relative to the field using the handles and place the sensor frame on the top surface of the field at a data collection point, thereby allowing the tilled floor sensing assembly to capture data indicative of the profile of the tilled floor. Alternatively, the sensor frame may correspond to any other suitable device configured to support the tilled floor sensing assembly relative to the top surface of the field, such as an unpowered vehicle (e.g., a cart) or a powered vehicle (e.g., an unmanned ground vehicle).

In accordance with aspects of the present subject matter, the tilled floor sensing assembly may include a plurality of pins, a force sensor provided in operative association with each pin, and a position sensor provided in operative association with each pin. More specifically, the plurality of pins may be extended relative to the sensor frame such that each pin penetrates the top surface of the field. As the pins extend, each force sensor may be configured to capture data indicative of the force being applied to a given pin, while each position sensor may be configured to capture data indicative of the position of a given pin relative to the sensor frame body. Such force and position data may, in turn, be indicative of the profile of the tilled floor of the field. For example, in one embodiment, when a given pin contacts the top surface, the force being applied to the given pin may spike. Thereafter, when the given pin contacts the tilled floor, the force being applied to the given pin may spike again. In this respect, the position of each pin relative to the sensor frame body when the force acting on such pin spikes a second time may be indicative of the profile of the tilled floor. Thus, independently monitoring the forces and positions of each pin of the plurality of pins may allow the profile of the tilled floor to be determined.

Figure 1:
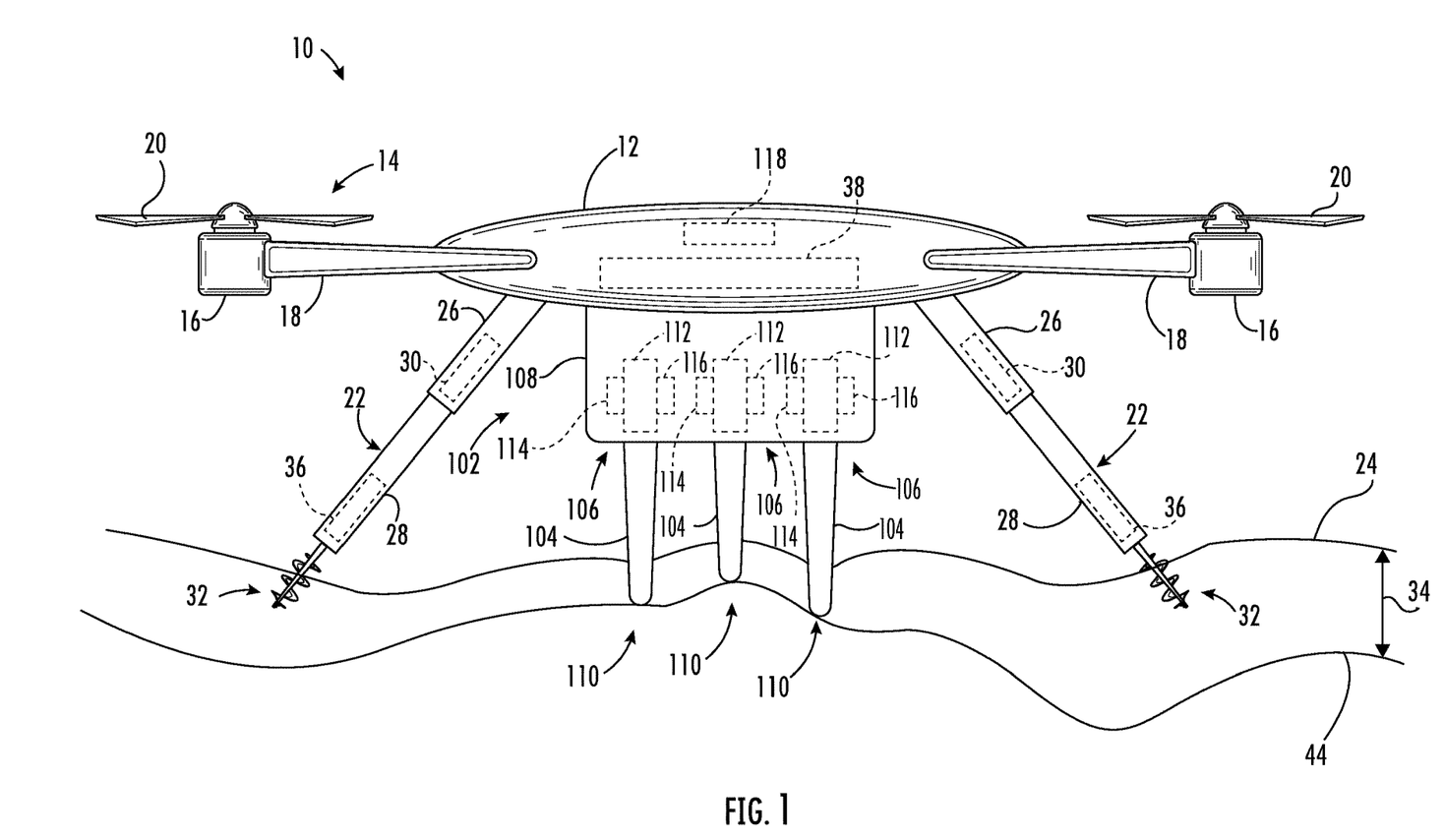
FIG. 1 illustrates a front view of one embodiment of a sensor frame supporting a tilled floor sensing assembly in accordance with aspects of the present subject matter, particularly illustrating the sensor frame configured as an unmanned aerial vehicle (UAV)

Referring now to the drawings, FIG. 1 illustrates a front view of one embodiment of a sensor frame 10 in accordance with aspects of the present subject matter. As shown, in several embodiments, the sensor frame 10 is configured as an unmanned aerial vehicle (UAV). In such embodiments, the sensor frame 10 may be configured to be flown over a field (e.g., an agricultural field) and landed at one or more data collection points within the field. As such, the sensor frame 10 may generally correspond to any suitable aerial vehicle capable of unmanned flight, such as any UAV capable of controlled vertical, or nearly vertical, takeoffs and landings. For example, in the illustrated embodiment, the sensor frame 10 is configured as a quadcopter. However, in alternative embodiments, the sensor frame 10 may be configured as any other multi-rotor aerial vehicle, such as a tricopter, hexacopter, or octocopter. In further embodiments, the sensor frame 10 may be configured as a single-rotor helicopter or a fixed wing, hybrid vertical takeoff and landing aircraft.

As shown, the sensor frame 10 may include various components that permit the sensor frame 10 to be flown across the field and landed at a data collection point. Specifically, in several embodiments, the sensor frame 10 may include a body or frame 12 that supports a propulsion system 14. For example, in one embodiment, the propulsion system 14 may include four motors 16 (two are shown in FIG. 1), with each motor 16 coupled to the body 12 via a support arm 18. Each motor 16 may, in turn, be configured to rotationally drive an associated propeller 20. However, in alternative embodiments, the propulsion system 14 may have any other suitable configuration. For example, the propulsion system 14 may include fewer or more than four motors 16 and associated propellers 20.

Furthermore, the sensor frame 10 may include a plurality of legs 22 configured to support the body 12 relative to the top surface 24 of the field when the sensor frame 10 is in the landed position. For example, in one embodiment, the sensor frame 10 may include four legs 22 (two are shown in FIG. 1) extending outward from the body 12. However, in alternative embodiments, the sensor frame 10 may include any other suitable number of legs 22. Additionally, in several embodiments, the legs 22 may be configured to telescope or otherwise extend and retract in a manner that allows the orientation of the body 12 relative to the top surface 24 of the field to be adjusted. Specifically, in such embodiments, each leg 22 may include a first leg portion 26 coupled to the body 12 and a second leg portion 28 configured to move relative to the first leg portion 26. In this respect, a leg actuator 30 (e.g., an electric motor) may be configured to extend and retract the second leg portion 28 relative to the first leg portion 26, thereby increasing and decreasing the length of the corresponding leg 22. As will be described below, in one embodiment, the lengths of each leg 22 may be independently adjusted to level the body 12 of the sensor frame 10 relative to the top surface 24 of the field. However, in alternative embodiments, the legs 22 may have any other suitable configuration. For instance, in one embodiment, the legs 22 may be non-telescoping and have a fixed length.

Additionally, the sensor frame 10 may include one or more anchoring devices 32. In general, the anchoring device(s) 32 may be configured to penetrate through the top surface 24 and engage the soil within a seedbed (indicated by arrow 34) of the field, thereby anchoring the sensor frame 10 relative to the field and maintaining the sensor frame 10 in its landed position. Specifically, in several embodiments, one anchoring device 32 may be provided in operative association with each leg 22 of the sensor frame 10. For example, in such embodiments, each anchoring device 32 may be coupled to a distal end of a given leg 22, with the distal end being opposed to a proximal end of the leg 22 that is coupled to the body 12. In one embodiment, each anchoring device 32 may correspond to an auger-type device. For example, in such an embodiment, an anchoring device actuator 36 (e.g., an electric motor) may be configured to rotationally drive a corresponding anchoring device 32 relative to the top surface 24 to allow the anchoring device 32 to engage the soil of the seedbed 34 and anchor the sensor frame 10 relative to the field. However, in alternative embodiments, the anchoring device(s) 32 may be configured as any other suitable device(s) configured to anchor the sensor frame 10 relative to the field. Furthermore, the anchoring device(s) may be positioned at any other suitable location(s) on the sensor frame 10. Additionally, the sensor frame 10 may include any other suitable number of anchoring devices 32.

Moreover, in several embodiments, the sensor frame 10 may include a levelness sensor 38. In general, the levelness sensor 38 may be configured to capture data indicative of the orientation of the body 12 of the sensor frame 10, such as relative to the direction of gravity or the top surface of the field (e.g., the top surface 24). In this respect, and as will be described below, the data captured by the levelness sensor 38 may be used to control the operation of the leg actuators 30 when leveling or otherwise adjusting the orientation of the body 12 of the sensor frame 10. As such, the levelness sensor 38 may correspond to any suitable sensing device(s) configured to capture data indicative of the orientation of the body 12 of the sensor frame 10. For example, in one embodiment, the levelness sensor 38 may correspond to an inclinometer. However, in alternative embodiments, the levelness sensor 38 may correspond to any other suitable sensing device(s), such as a gyroscope.

Figure 2:
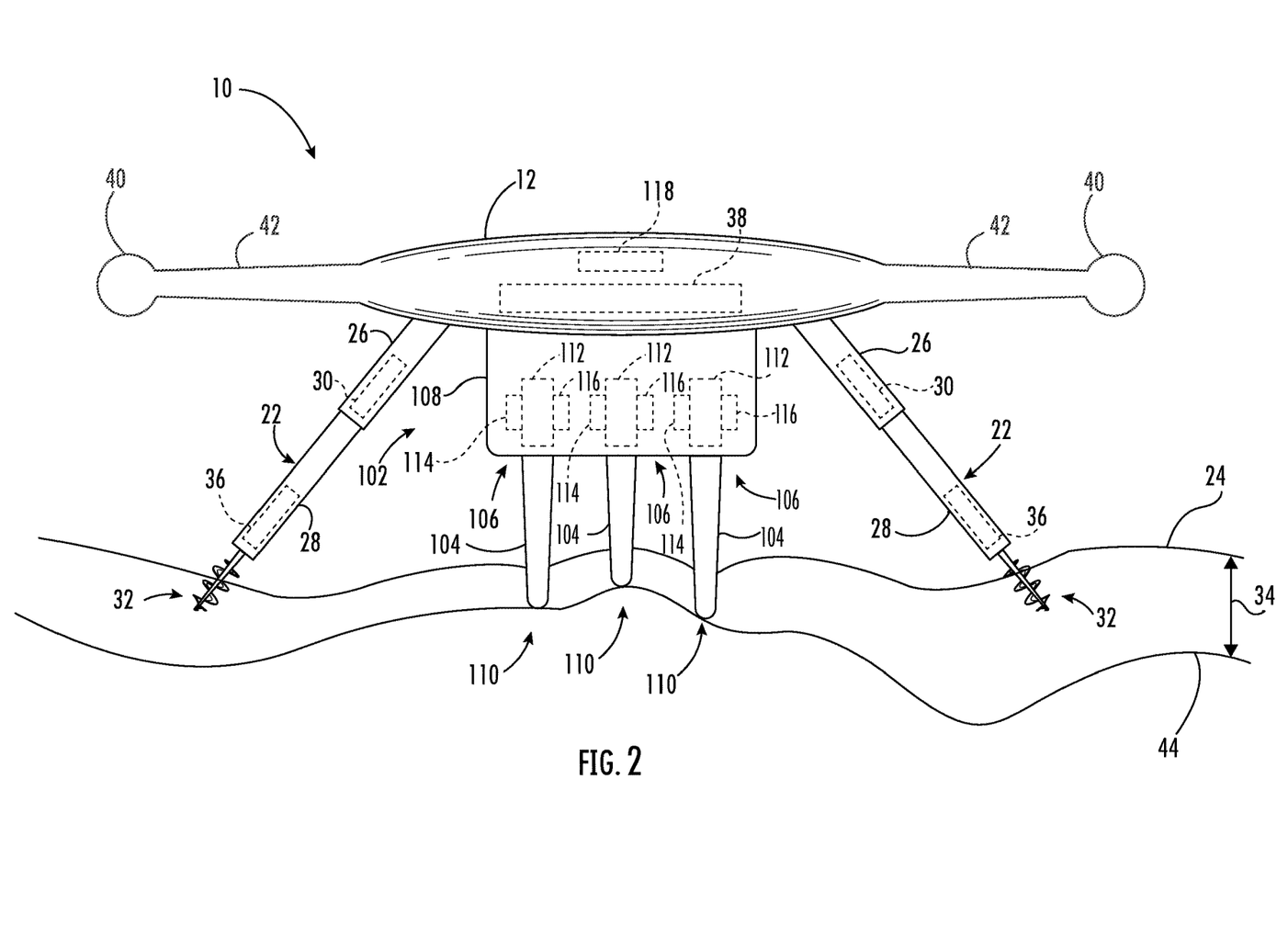
FIG. 2 illustrates a front view of another embodiment of a sensor frame supporting a tilled floor sensing assembly in accordance with aspects of the present subject matter, particularly illustrating the sensor frame configured as a hand-held device having handles that permit an operator to move the sensor frame relative to a field.

Referring now to FIG. 2, a front view of another embodiment of a sensor frame 10 is illustrated in accordance with aspects of the present subject matter. As shown, in the illustrated embodiment, the sensor frame 10 is configured as a hand-held device. In general, the sensor frame 10 shown in FIG. 2 is configured substantially similar to the sensor frame 10 shown in FIG. 4. For example, the sensor frame 10 shown in FIG. 2 includes a body or frame 12 and a plurality of legs 22 configured to support the body 12 relative to the top surface (e.g., the top surface 24) of the field. However, unlike the sensor frame 10 shown in FIG. 1, the sensor frame 10 shown in FIG. 2 does not include a propulsion system 14. Instead, the sensor frame 10 shown in FIG. 2 includes a plurality of handles 40 configured to permit an operator to move the sensor frame 10 relative to the field. For example, in one embodiment, the sensor frame 10 may include two handles 40, with each handle 40 coupled to the body 12 via a support arm 42. As such, the operator may be able to lift the sensor frame 10 using the handles 40 and carry the sensor frame 10 relative to the field to one or more data collection points within the field. Once at a data collection point, the operator may place the sensor frame 10 on the top surface 24, with the legs 22 supporting the body 10 relative to the top surface 24. Additionally, in one embodiment, after placement at a data collection point, anchoring device(s) 32 may anchor the sensor frame 10 relative to the field and maintain the sensor frame 10 in its landed position.

It should be further appreciated that the configurations of the sensor frame 10 described above and shown in FIGS. 1 and 2 are provided only to place the present subject matter in an exemplary field of use. Thus, it should be appreciated that the present subject matter may be readily adaptable to any manner of sensor frame configuration. For example, in one embodiment, the sensor frame 10 may be configured as a suitable vehicle, such as an unpowered vehicle (e.g., a wheeled cart) or a powered vehicle (e.g., an unmanned ground vehicle (UGV)).

Referring to FIGS. 1 and 2, a tilled floor sensing assembly 102 may be supported on the sensor frame 10. In general, the tilled floor sensing assembly 102 may be configured to capture data indicative of the profile of the tilled floor of the field at a data location point (i.e., the location where the sensor frame 10 has landed or is placed by the operator). As will be described below, a computing system (e.g., an onboard controller of the sensor frame 10 and/or a controller of a remote device, such as a laptop) may be configured to receive the data captured by the tilled floor sensing assembly 102. Thereafter, the computing system may be configured to analyze the received data to determine or estimate the profile of the tilled floor at the data collection point. The tilled floor of the field may, in turn, correspond to the floor or bottom surface of the layer of tilled soil created by a tillage operation. In certain instances, the tilled floor may correspond to the seedbed floor. However, in other instances, the tilled floor may be below the seedbed floor.

In several embodiments, the tilled floor sensing assembly 102 may be supported on the body 12 of the sensor frame 10. Specifically, in one embodiment, the tilled floor sensing assembly 102 may be installed on the underside of the sensor frame body 12. In such an embodiment, the tilled floor sensing assembly 102 may be positioned at a central location on the sensor frame 10 such that the assembly 102 is located between the legs 22. Such central positioning may minimize the effect of small variations in the levelness of the sensor frame 10 on the data being captured by the tilled floor sensing assembly 102. However, in alternative embodiments, the tilled floor sensing assembly 102 may be positioned at any other suitable location on the sensor frame 10. For example, in one embodiment, the tilled floor sensing assembly 102 may be coupled to a support arm (not shown) extending outward from the body 12.

Additionally, the tilled floor sensing assembly 102 may include a plurality of pins 104 configured to be extended and retracted relative to the body 12 of the sensor frame 10. As will be described below, such extension of the pins 104 may allow the pins 104 to penetrate through the top surface 24 and the soil of the seedbed 34 until reaching a tilled floor 44 of the seedbed 34. More specifically, in several embodiments, each pin 104 may include a first end 106 positioned proximal to the body 12 of the sensor frame 10. For example, the first ends 106 of the pins 104 may be positioned within a housing 108 of the tilled floor sensing assembly 104. Furthermore, each pin 104 may include an opposed, second end 110 positioned distal to the body 12, with the second end 110 configured to penetrate the top surface 24 and the soil within the seedbed 34 as the pin 104 is extended relative to the sensor frame body 12. In one embodiment, the second ends 110 of the pins 104 may be blunted to prevent the pins 104 from penetrating through the tilled floor 40. For example, in such an embodiment, the second ends 110 of the pins 104 may have a hemispherical or otherwise rounded tip. Moreover, in one embodiment, the tilled floor sensing assembly 102 may include four pins 104 (three are shown in FIG. 1). However, in alternative embodiments, the tilled floor sensing assembly 102 may include two pins 104, three pins 104, or five or more pins 104.

The pins 104 may be arranged in any suitable manner. For example, in one embodiment, the pins 104 may be arranged in a line extending generally perpendicular relative to the direction of travel of a tillage implement (not shown) that performed the tillage operation forming the tilled floor. However, in other embodiments, the pins 104 may be arranged at any other suitable angle (e.g., at a forty-five-degree angle) relative to the direction of travel of the tillage implement or in another geometric configuration (e.g., a diamond shape).

In addition, the pins 104 of the tilled floor sensing assembly 102 may be spaced apart from one another. Such a spaced apart relationship may allow the pins 104 to penetrate the soil in several different positions at the data collection point, thereby allowing the tilled floor sensing assembly 102 to collect data indicative of the tilled floor at several different positions at the data collection point. As will be described below, collecting tilled floor data at several different positions within the data collection point may allow the profile (e.g., a 2D or 3D representation) of the tilled floor to be determined. For example, in one embodiment, the pins 104 may be spaced apart in a rectangular arrangement. However, in alternative embodiments, the pins 104 may be spaced apart in any other suitable manner.

Furthermore, the tilled floor sensing assembly 102 may include a plurality of pin actuators 112. In general, each pin actuator 112 may be configured to extend and retract a corresponding pin 104 relative to the sensor frame body 12. Such extension may, in turn, cause the pins 104 to penetrate through the top surface 24 and the soil within the seedbed 34. As will be described below, the positions of the pins 104 relative to the body 12 and the forces being applied to the pins 104 may be monitored as the pins 104 are extended. Such position and force data may, in turn, be indicative of the profile of the tilled floor 40. Retraction of the pins 104 may remove the pins 104 from the soil after the position and force data has been collected, thereby allowing the sensor frame 10 to take off from its landed position or be lifted and moved by the operator. Specifically, in several embodiments, one pin actuator 112 may be provided in operative association with a corresponding pin 104. In this respect, each pin actuator 112 may be configured to extend and retract one of the pins 104. As such, the pins 104 may be independently extended and retracted relative to sensor frame body 12. For example, when one pin 104 contacts the tilled floor 40, the corresponding pin actuator 112 may halt further extension of such pin 104. However, the other pin actuators 112 may continue extend the corresponding pins 104 until such pins 102 contact the tilled floor 40. Thus, one or more pins 104 may continue to be extended after extension of another pin(s) 104 has been halted. As will be described below, such independent extension and retraction of the pins 104 may allow data indicative of the profile(s) of the tilled floor 40 to be captured.

The pin actuators 112 may correspond to any suitable devices configured to extend and retract the pins 104 relative to the sensor frame body 12. For example, in one embodiment, the pin actuators 112 may correspond to electric linear actuators or solenoids positioned within the housing 108 of the tilled floor sensing assembly 102. In such an embodiment, the pins 104 may be positioned entirely (or substantially entirely) within the housing 108 when fully retracted. As such, each pin actuator 112 may be configured to extend a corresponding pin 104 outward (e.g., downward) through a corresponding aperture (not shown) in the housing 108 for eventual contact with the seedbed 40. After the position and force data has been collected, the pin actuators 112 may retract the pins 104 into the housing 108. However, in alternative embodiments, the pin actuators 112 may be configured as any other suitable actuators (e.g., stepper motors, pneumatic cylinders, hydraulic cylinders, and/or the like) and may be positioned at any other suitable locations on the UAV 10.

Moreover, the tilled floor sensing assembly 102 may include a plurality of position sensors 114. Specifically, in several embodiments, each position sensor 114 may be provided in operative association within one of the pins 104. In this respect, as each pin 104 is extended and retracted, the corresponding position sensor 114 may be configured to capture data indicative of the position or location of the pin 104 relative to the sensor frame body 12. As will be described below, such position data may permit the profile of the tilled floor 40 to be determined. Additionally, the position sensors 114 may correspond to any suitable sensing devices capable of capturing data indicative of the positions of the pins 104 relative to the sensor frame body 12. For example, in one embodiment, each position sensors 114 may correspond to a Hall Effect sensor. However, in alternative embodiments, the position sensors 114 may correspond to any other suitable types of sensors or sensing devices, such as linear variable differential transformers (LVDTs).

In addition, the tilled floor sensing assembly 102 may include a plurality of force sensors 116. Specifically, in several embodiments, each force sensor 116 may be provided in operative association within one of the pins 104. In this respect, as each pin 104 is extended and retracted, the corresponding force sensor 116 may be configured to capture data indicative of the force or load being applied to the pin 104 (e.g., by the soil of the seedbed 34). As will be described below, such force data may permit the profile(s) of the tilled floor 44 to be determined. Additionally, the force sensors 116 may correspond to any suitable sensing devices capable of capturing data indicative of the forces being applied to the pins 104. For example, in one embodiment, each force sensor 116 may correspond to a load cell. However, in alternative embodiments, the force sensors 116 may correspond to any other suitable types of sensors or sensing devices, such as strain gauges.

In one embodiment, as shown in FIG. 1, a location sensor 118 may be provided in operative association with the sensor frame 10. In general, the location sensor 118 may be configured to determine the current location of the sensor frame 10 using a satellite navigation positioning system (e.g. a GPS system, a Galileo positioning system, the Global Navigation satellite system (GLONASS), the BeiDou Satellite Navigation and Positioning system, and/or the like). In such an embodiment, the location determined by the location sensor 118 may be transmitted to a computing system (e.g., in the form coordinates) and stored within the computing system's memory for subsequent processing and/or analysis. Thereafter, the determined location from the location sensor 118 may be used to geo-locate the sensor frame 10 within the field.

Figure 3:
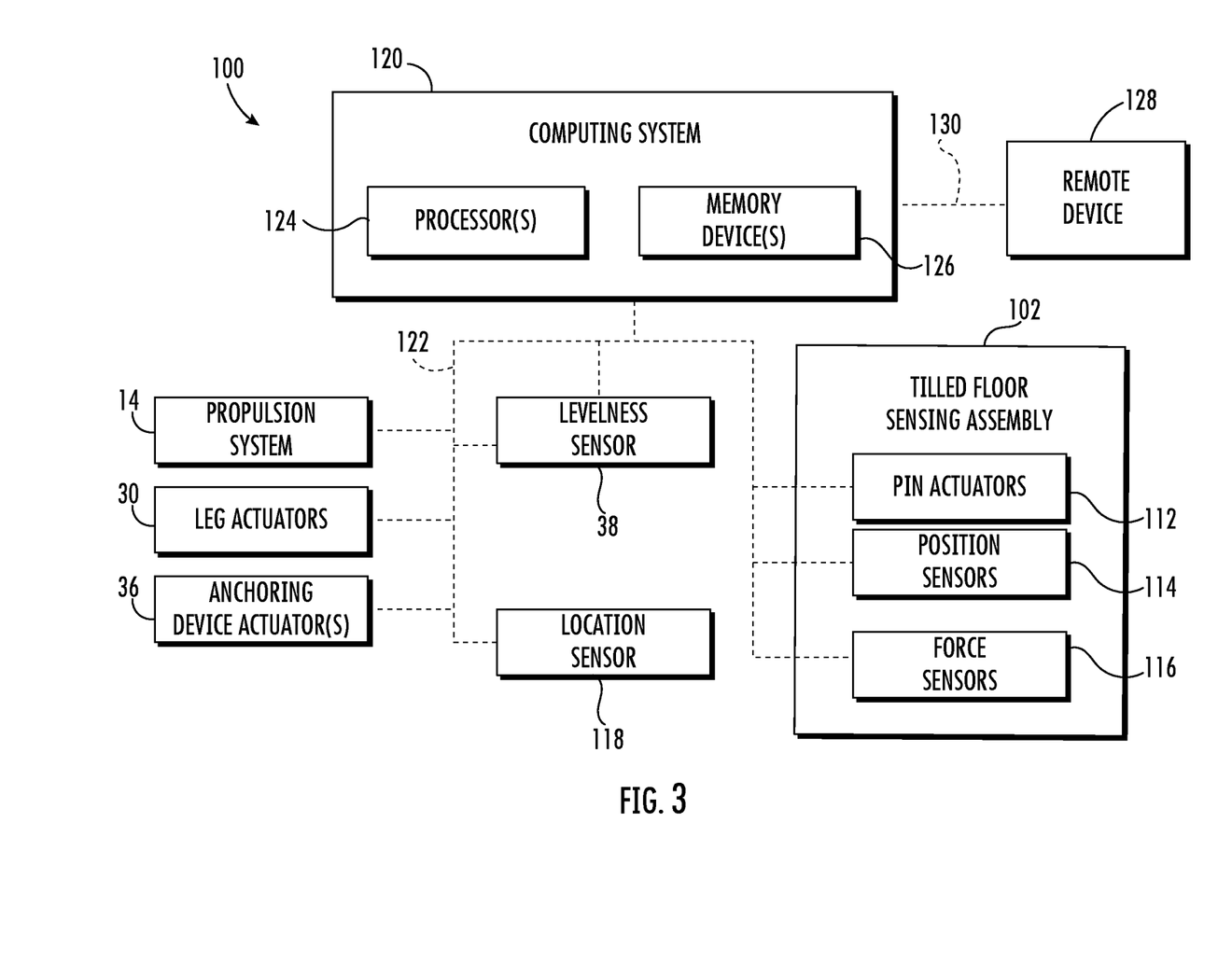
FIG. 3 illustrates a schematic view of one embodiment of a system for monitoring tilled floor conditions within a field in accordance with aspects of the present subject matter.

Referring now to FIG. 3, a schematic view of one embodiment of a system 100 for monitoring tilled floor conditions within a field is illustrated in accordance with aspects of the present subject matter. In general, the system 100 will be described herein with reference to the sensor frame 10 described above with reference to FIGS. 1 and 2. However, it should be appreciated by those of ordinary skill in the art that the disclosed system 100 may generally be utilized with sensor frames having any other suitable sensor frame configuration.

As shown in FIG. 3, the system 100 may include a computing system 120 communicatively coupled to one or more components of the sensor frame 10 and/or the tilled floor sensing assembly 102 to allow the operation of such components to be electronically or automatically controlled by the computing system 120. For instance, the computing system 120 may be communicatively coupled to the propulsion system 14 (e.g., via the communicative link 122). As such, the computing system 120 may be configured to control the operation of the propulsion system 14 such that the sensor frame 10 is flown across a field and landed at a data collection point. Moreover, the computing system 120 may be communicatively coupled to the leg actuators 30, the anchoring device actuator(s) 36, and the levelness sensor 38 (e.g., via the communicative link 122). In this respect, based on data received from the levelness sensor 38, the computing system 120 may be configured to control the operation of the actuators 30, 36 to level and anchor the sensor frame 10 relative to the top surface 24. Furthermore, the computing system 120 may be communicatively coupled to the pin actuators 112 (e.g., via the communicative link 122). Thus, the computing system 120 may be configured to initiate adjustment of the positions of the pins 104 relative to the sensor frame 10 by controlling the operation of the pin actuators 112. Additionally, the computing system 120 may be communicatively coupled to the position sensors 112, the force sensors 114, the location sensor 118, and/or any other suitable components of the sensor frame 10 and/or the tilled floor sensing assembly 102 (e.g., via the communicative link 122).

In general, the computing system 120 may comprise one or more processor-based devices, such as a given controller or computing device or any suitable combination of controllers or computing devices. Thus, in several embodiments, the computing system 120 may include one or more processor(s) 124 and associated memory device(s) 126 configured to perform a variety of computer-implemented functions. As used herein, the term "processor" refers not only to integrated circuits referred to in the art as being included in a computer, but also refers to a controller, a microcontroller, a microcomputer, a programmable logic circuit (PLC), an application specific integrated circuit, and other programmable circuits. Additionally, the memory device(s) 126 of the computing system 120 may generally comprise memory element(s) including, but not limited to, a computer readable medium (e.g., random access memory RAM)), a computer readable non-volatile medium (e.g., a flash memory), a floppy disk, a compact disk-read only memory (CD-ROM), a magneto-optical disk (MOD), a digital versatile disk (DVD) and/or other suitable memory elements. Such memory device(s) 126 may generally be configured to store suitable computer-readable instructions that, when implemented by the processor(s) 124, configure the computing system 120 to perform various computer-implemented functions, such as one or more aspects of the methods and algorithms that will be described herein. In addition, the computing system 120 may also include various other suitable components, such as a communications circuit or module, one or more input/output channels, a data/control bus and/or the like.

The various functions of the computing system 120 may be performed by a single processor-based device or may be distributed across any number of processor-based devices, in which instance such devices may be considered to form part of the computing system 120. For instance, the functions of the computing system 120 may be distributed across multiple application-specific controllers, such as an onboard UAV controller, a navigation controller, a controller(s)/computing device(s) of a remote device(s) (e.g., a laptop or Smartphone), and/or the like.

In one embodiment, the system 100 may include a remote device 128 configured to receive and/or store data associated with profile of the tilled floor. For example, in one embodiment, the remote device 128 may correspond to a remote database server (e.g., positioned within a farm management office). In such an embodiment, the remote device 128 may include one or more processor(s) and associated memory device(s) configured to perform a variety of computer-implemented database server functions. Such memory device(s) may generally be configured to store suitable computer-readable instructions that, when implemented by the processor(s), configure the remote device 128 to perform various computer-implemented database server functions. Furthermore, a communicative link or interface 130 (e.g., a data bus) may be provided between the remote device 128 and the computing system 120 to allow the remote device 128 and the computing system 120 to communicate via any suitable communications protocol (e.g., Wi-Fi, 3G, 4G, LTE, and/or the like). However, in alternative embodiments, the remote device 128 may correspond to any suitable device(s) configured to receive and/or store data associated with profile(s) of the tilled floor, such as a laptop, a tablet, a Smartphone, a work vehicle controller, an agricultural implement controller, a cloud-based computing system, and/or the like. Alternatively, in some embodiments, the remote device 128 may form part of the computing system 120.

In several embodiments, the sensor frame 10 (and the tilled floor sensing assembly 102 supported thereon) may be positioned on the top surface (e.g., the top surface 24) of the field at a data collection point. As mentioned above, in some embodiments, the sensor frame 10 may be configured as a UAV. In such embodiments, the computing system 120 may be configured to control the operation of the sensor frame 10 such that the sensor frame 10 is flown over the field and landed at the data collection point. Specifically, the computing system 120 may be configured to access data associated with the location(s) of one or more data collection points within the field. For example, in one embodiment, the computing system 120 may be configured to receive the coordinates for one or more data collection points from a remote device (e.g., from the remote device 128 via the communicative link 130). Alternatively, the computing system 120 may be configured to access or retrieve the coordinates for one or more data collection points stored within its memory device(s) 126. Thereafter, the computing system 120 may be configured to control the operation of one or more components of the sensor frame 10 (e.g., the propulsion system 14) such that the sensor frame 10 is flown across the field and landed the data point collection point. Once in the landed position, the sensor frame 10 may be supported relative to the top surface of the field by its legs 22. In other embodiments, as described above, the sensor frame 10 may be configured as a hand-held device. In such embodiments, the operator may move the sensor body 10 relative to the field using the handle(s) 40 and place the sensor frame 10 on the top surface of the field at a data collection point. Additionally, the data collection point(s) may correspond to any suitable location(s) within the field at which the tilled floor sensing assembly 102 can capture data indicative of the profile of the tilled floor.

In one embodiment, after the sensor frame 10 has landed at a data collection point, the computing system 120 may be configured to initiate leveling of the sensor frame 10. More specifically, it may be necessary for the body 12 of the sensor frame 10 to be level (or substantially level) for the tilled floor sensing assembly 102 to capture accurate data associated with the profile of the tilled floor. When the body 12 is out of level, the pins 104 of the tilled floor sensing assembly 102 may penetrate the soil at angle, thereby providing inaccurate indication of the tilled floor profiles. In this respect, as mentioned above, the sensor frame 10 may include a levelness sensor 38 configured to capture data indicative of the orientation of the body 12 of the sensor frame 10. As such, the computing system 120 may be configured to receive levelness data from the levelness sensor 38 (e.g., via the communicative link 122) after the sensor frame 10 has positioned at the data collection point. Thereafter, the computing system 120 may be configured to determine the orientation of the body 12 (e.g., relative to the direction of gravity or the top surface of the field) based on the received levelness data. When the orientation of the sensor frame body 12 falls outside of a predetermined levelness range (thereby indicating that the body 12 is out of level), the computing system 120 may be configured to control the operation of one or more leg actuators 30 of the sensor frame 10. For example, the computing system 120 may be configured to transmit control signals to the leg actuator(s) 30 (e.g., via the communicative link 122) instructing the actuator(s) 30 to extend and/or retract the corresponding legs 22 in a manner that levels the sensor frame body 12.

Furthermore, in one embodiment, after the sensor frame 10 is positioned on the top surface at a data collection point, the computing system 120 may be configured to initiate anchoring of the sensor frame 10 to the field. More specifically, in certain instances, when the pins 104 of the tilled floor sensing assembly 102 are extended into the seedbed (e.g., the seedbed 34), the forces exerted on the pins 104 by the soil may cause the sensor frame body 12 to lift off the top surface of the field or become out of level, thereby resulting inaccurate data. In this respect, as described above, the sensor frame 10 may include one or more anchoring devices 32 that anchor or otherwise secure the sensor frame 10 to the seedbed. As such, once the sensor frame 10 is positioned on the top surface at a data collection point, the computing system 120 may be configured to control the operation of the anchoring device actuator(s) 36 to secure the sensor frame 10 to the seedbed. For example, the computing system 120 may be configured to transmit control signals to the anchoring device actuator(s) 36 (e.g., via the communicative link 122) instructing the actuator(s) 36 to rotationally drive the anchoring device(s) 32 such that the anchoring device(s) 32 engage the soil of the seedbed in a manner that anchors the sensor frame 10 to the field. The computing system 120 may be configured to initiate anchoring of the sensor frame 10 to the field before or after the sensor frame 10 has been leveled.

In accordance with aspects of the present subject, the computing system 120 may be configured to control the operation of the tilled floor sensing assembly 102 such that the assembly 102 captures data indicative of the profile of the tilled floor (e.g., the tilled floor 40) at the location where the sensor frame 10 is positioned (e.g., the data collection point). As mentioned above, the tilled floor sensing assembly 102 may include a plurality of pins 104 configured to extend and retract relative to the sensor frame body 12. In this regard, after the sensor frame 10 has been leveled and/or anchored, the computing system 120 may be configured to control the operation of the tilled floor sensing assembly 102 to extend the pins 104 relative to the sensor frame body 12 such that the pins 104 to penetrate the top surface and through the soil of the seedbed before contacting the tilled floor. For example, the computing system 120 may be configured to transmit control signals to the pin actuators 112 (e.g., via the communicative link 122) instructing each actuator 112 to extend the corresponding pin 104. Moreover, as the pins 104 are extended, the computing system 120 may be configured to receive position data associated with the positions of the pins 104 relative to the sensor frame body 12 from the position sensors 114 (e.g., via the communicative link 122) and force data associated with the forces being applied to the pins 104 from the force sensors 116 (e.g., via the communicative link 122).

Additionally, the computing system 120 may be configured to determine the profile of the tilled floor of the field. As described above, the position and force data may be indicative of the profile of the tilled floor of the field. In this respect, the computing system 120 may be configured to process or analyze the received position data and force data to determine or estimate the tilled floor profile of the field at the data collection point. For instance, the computing system 120 may include a look-up table(s), suitable mathematical formula, and/or an algorithm(s) stored within its memory device(s) 126 that correlates the received position and force data to the tilled floor profile of the field. After the tilled floor profile has been determined (or the associated position and force data has been captured), the computing system 120 may initiate retraction of the pins 104 from the seedbed. For example, the computing system 120 may be configured to transmit control signals to the pin actuators 112 instructing the actuators 112 to retract the pins 104 relative to the sensor frame body 12.

As mentioned above, the positions of and the forces acting on the pins 104 as the pins 104 are extended into the seedbed may be indicative of the profile of the tilled floor. More specifically, as the pins 104 are extended from their retracted positions (e.g., retracted within the housing 108 of the seedbed assembly 102), little or no load is initially applied to the pins 104. When a given pin 104 contacts the top surface, the load applied to the given pin 104 spikes or otherwise increases substantially as the soil is now applying a force of the given pin 104. In this respect, when the load applied to the given pin 104 spikes, the computing system 120 may determine that the given pin has contacted the top surface. Furthermore, after the given pin 104 has pierced the top surface and is penetrating through the soil of the seedbed, the force applied to the given pin 104 increases as the penetration depth of the given pin 104 increases. However, when the given pin 104 contacts the tilled floor, the load applied to the given pin 104 spikes or otherwise increases substantially a second time as the given pin 104 is generally unable to pierce the tilled floor (e.g., due to its blunted second end 110). As such, when the load applied to the given pin 104 spikes a second time, the computing system 120 may determine that the given pin has contacted the tilled floor. Based on the position of the given pin 104 relative to the sensor frame body 12 when the force applied to the given pin 104 spikes the second time, the computing system 120 may determine the position of the tilled floor relative to the body 12.

By determining the positions of the tilled floor at the location each pin 104 of the tilled floor sensing assembly 102, the computing system 120 may be able to determine or estimate the profile of the tilled floor of the field at the data collection point. More specifically, as described above, the pins 104 are independently extendable and spaced apart from each other. For example, when one pin 104 contacts the tilled floor, each other pin 104 will continue to be extended until it too contacts the tilled floor. In this respect, by using a plurality of independently extendible, spaced apart pins 104, the tilled floor sensing assembly 102 may be able to capture data indicative of the tilled floor at multiple different positions when the sensor frame 10 has landed at the data collection point. Such multiple tilled floor measurements may allow the computing system 120 to determine a profile (e.g., a 2D or 3D representation) of the tilled floor at the data collection point.

In one embodiment, the computing system 120 may be configured to determine the average depth of the tilled floor at the data collection point(s). As described above, the computing system 120 may be configured to determine the profile of the tilled floor at the data collection point(s) based on data received from the tilled floor sensing assembly 102. In this respect, the controller 102 may be configured to determine or estimate the average depth of the tilled floor of the field based on the determined profile of the tilled floor. For instance, the computing system 120 may include a look-up table(s), suitable mathematical formula, and/or an algorithm(s) stored within its memory device(s) 126 that calculates the average depth of the tilled floor of the field from the determined tilled floor profile.

Moreover, the computing system 120 may be configured to geo-locate determined top surface and/or tilled floor profiles. Specifically, as described above, in one embodiment, the sensor frame 10 may include a location sensor 118 installed thereon. In such an embodiment, the computing system 120 may be configured to receive location data (e.g., coordinates) from the location sensor 118 when the sensor frame 10 has landed on the field (e.g., at a data collection point). Thereafter, the computing system 120 may be configured to correlate or tag the determined tilled floor profile (or the associated position and/or force data) with the received location data. Alternatively, the computing system 120 may correlate or tag the determined tilled floor profile with the received/accessed coordinates associated with the data collection point at which such profile was determined.

Additionally, the computing system 120 may be configured to transmit the determined tilled floor profile to the remote device 128. As described above, the computing system 120 may be communicatively coupled to the remote device 128. In this respect, the computing system 120 may be configured to transmit the determined tilled floor profile (and/or the received data from the tilled floor sensing assembly 102) to the remote device 128 (e.g., via the communicative link 130). Thereafter, the tilled floor profile may be displayed to an operator on a display screen (not shown) of the remote device 128. In addition (or as an alternative thereto), the tilled floor profile may be stored within the memory (not shown) of the remote device 128, such as for use during a subsequent agricultural operation.

Figure 4:
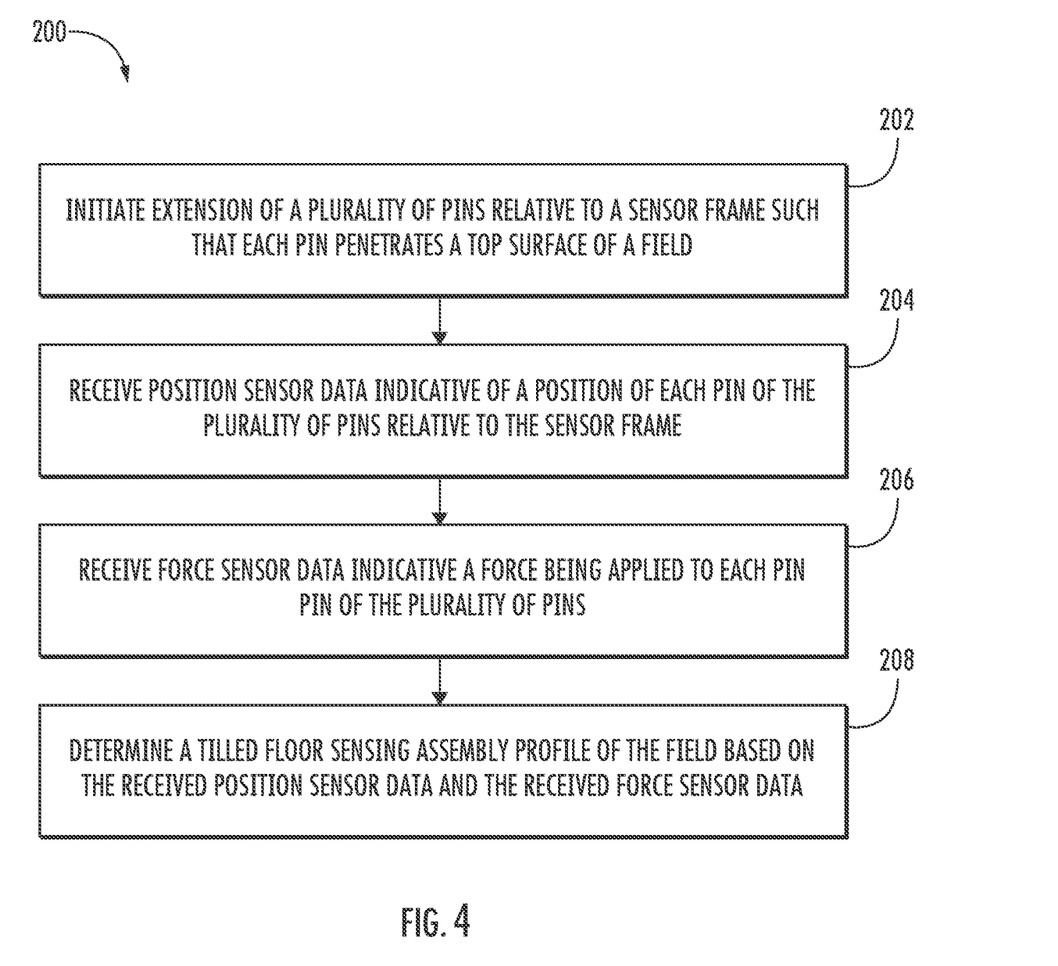
FIG. 4 illustrates a flow diagram of one embodiment of a method for monitoring tilled floor conditions within a field in accordance with aspects of the present subject matter.

Referring now to FIG. 4, a flow diagram of one embodiment of a method 200 for monitoring tilled floor conditions within a field is illustrated in accordance with aspects of the present subject matter. In general, the method 200 will be described herein with reference to the sensor frame 10 and the system 100 described above with reference to FIGS. 1-3. However, it should be appreciated by those of ordinary skill in the art that the disclosed method 200 may generally be implemented with any sensor frame having any suitable sensor frame configuration and/or within any system having any suitable system configuration. In addition, although FIG. 4 depicts steps performed in a particular order for purposes of illustration and discussion, the methods discussed herein are not limited to any particular order or arrangement. One skilled in the art, using the disclosures provided herein, will appreciate that various steps of the methods disclosed herein can be omitted, rearranged, combined, and/or adapted in various ways without deviating from the scope of the present disclosure.

As shown in FIG. 4, at (202), the method 200 may include initiating, with a computing system, extension of a plurality of pins relative to the sensor frame such that each pin penetrates a top surface of the field. For instance, as described above, the computing device 120 may be configured to control the operation of the pin actuators 112 to initiate extension of the pins 104 of the tilled floor sensing assembly 102 relative to the sensor frame body 12 such that each pin 104 penetrates a top surface (e.g., the top surface 24) of the field.

Additionally, at (204), the method 200 may include receiving, with the computing system, position sensor data indicative of a position of each pin of the plurality of pins relative to the sensor frame. For instance, as described above, the computing device 120 may be configured to receive position data indicative of the position of each pin 104 relative to the sensor frame body 12 from the corresponding position sensor 114 of the tilled floor sensing assembly 102.

Moreover, as shown in FIG. 4, at (206), the method 200 may include receiving, with the computing system, force sensor data indicative a force being applied to each pin of the plurality of pins. For instance, as described above, the computing system 120 may be configured to receive force data indicative of the force applied to each pin 104 from the corresponding force sensor 116 of the tilled floor sensing assembly 102.

Furthermore, at (208), the method 200 may include determining, with the computing system, a tilled floor profile of the field based on the received position sensor data and the received force sensor data. For instance, as described above, the computing device 120 may be configured to determine the tilled floor profile of the field based on the position data received from the position sensors 114 and the force data received from the force sensors 116.

It is to be understood that the steps of the method 200 are performed by the computing system 120 upon loading and executing software code or instructions which are tangibly stored on a tangible computer readable medium, such as on a magnetic medium, e.g., a computer hard drive, an optical medium, e.g., an optical disc, solid-state memory, e.g., flash memory, or other storage media known in the art. Thus, any of the functionality performed by the computing system 120 described herein, such as the method 200, is implemented in software code or instructions which are tangibly stored on a tangible computer readable medium. The computing system 120 loads the software code or instructions via a direct interface with the computer readable medium or via a wired and/or wireless network. Upon loading and executing such software code or instructions by the computing system 120, the computing system 120 may perform any of the functionality of the computing system 120 described herein, including any steps of the method 200 described herein.

The term "software code" or "code" used herein refers to any instructions or set of instructions that influence the operation of a computer or controller. They may exist in a computer-executable form, such as machine code, which is the set of instructions and data directly executed by a computer's central processing unit or by a controller, a human-understandable form, such as source code, which may be compiled in order to be executed by a computer's central processing unit or by a controller, or an intermediate form, such as object code, which is produced by a compiler. As used herein, the term "software code" or "code" also includes any human-understandable computer instructions or set of instructions, e.g., a script, that may be executed on the fly with the aid of an interpreter executed by a computer's central processing unit or by a controller.

This written description uses examples to disclose the technology, including the best mode, and also to enable any person skilled in the art to practice the technology, including making and using any devices or systems and performing any incorporated methods. The patentable scope of the technology is defined by the claims, and may include other examples that occur to those skilled in the art. Such other examples are intended to be within the scope of the claims if they include structural elements that do not differ from the literal language of the claims, or if they include equivalent structural elements with insubstantial differences from the literal language of the claims.

The invention claimed is:

1. A system for monitoring tilled floor conditions within a field, the field including a seedbed formed of soil extending from a top surface of the field to a tilled floor, the system comprising:
   a sensor frame;
   a tilled floor sensing assembly supported on the sensor frame, the tilled floor sensing assembly comprising:
   a plurality of pins configured to be extended relative to the sensor frame such that each pin penetrates the top surface of the field and the soil forming the seedbed until reaching the tilled floor;

a plurality of position sensors, each position sensor configured to capture data indicative of a position of a given pin of the plurality of pins relative to the sensor frame; and a plurality of force sensors, each force sensor configured to capture data indicative of a force being applied to a given pin of the plurality of pins; and a computing system communicatively coupled to the plurality of position sensors and the plurality of force sensors, the computing system configured to determine a tilled floor profile of the field based on the data captured by the plurality of position sensors and the data captured by the plurality of force sensors together.

2. The system of claim 1, wherein each pin of the plurality of pins is independently mounted on the sensor frame.

3. The system of claim 1, further comprising:
a plurality of actuators, each actuator configured to extend a given pin of the plurality of pins relative to the sensor frame such that the given pin penetrates the top surface of the field.

4. The system of claim 1, wherein the computing system is further configured to determine an average depth of the tilled floor of the field based on the determined tilled floor profile.

5. The system of claim 1, wherein the computing system is further configured to transmit the determined tilled floor profile of the field to a remote device.

6. The system of claim 1, further comprising:
a location sensor installed on the sensor frame and communicatively coupled to the computing system, the computing system further configured to geo-locate the determined the tilled floor profile of the field.

7. The system of claim 1, the system further comprising:
a plurality of legs coupled to the sensor frame, the plurality of legs configured to support the sensor frame relative to the top surface of the field;

a plurality of actuators, each actuator configured to adjust a length of a given leg of the plurality of legs relative to the sensor frame; and a levelness sensor installed on the sensor frame and communicatively coupled to the computing system, the levelness sensor configured to capture data indicative of an orientation of the sensor frame, the computing system further configured to control an operation of the plurality of actuators to adjust the orientation of the sensor frame based on the data captured by the levelness sensor.

8. The system of claim 1, wherein each pin of the plurality of pins comprises a first end positioned proximal to the sensor frame and an opposed second end positioned distal to the sensor frame, the second end being blunted and configured to penetrate the top surface of the field.

9. The system of claim 1, wherein the sensor frame corresponds to an unmanned aerial vehicle (UAV), the UAV including a body and a plurality of legs coupled to the body, the plurality of legs configured to support the body relative to the top surface of the field when the UAV is in a landed position.

10. The system of claim 9, further comprising:
an anchoring device configured to engage soil within the field to anchor the UAV to the field when the UAV is in the landed position.

11. The system of claim 1, further comprising:
a handle coupled to the sensor frame, the handle configured to permit an operator to move the sensor frame relative to the field.

12. A method for monitoring tilled floor conditions within a field, the field including a seedbed formed of soil extending from a top surface of the field to a tilled floor, the method comprising:

initiating, with a computing system, extension of a plurality of pins relative to the sensor frame such that each pin penetrates the top surface of the field and the soil forming the seedbed until reaching the tilled floor;

receiving, with the computing system, position sensor data indicative of a position of each pin of the plurality of pins relative to the sensor frame;

receiving, with the computing system, force sensor data indicative a force being applied to each pin of the plurality of pins; and determining, with the computing system, a tilled floor profile of the field based on the received position sensor data and the received force sensor data.

13. The method of claim 12, wherein initiating extension of the plurality of pins comprises initiating, with the computing system, extension of the plurality of pins from the sensor frame.

14. The method of claim 12, wherein initiating extension of the plurality of pins comprises controlling, with the computing system, an operation of a plurality of actuators such that each actuator extends a given pin of the plurality of pins relative to the sensor frame.

15. The method of claim 12, further comprising:
determining, with the computing system, an average depth of the tilled floor of the field based on the determined tilled floor profile.

16. The method of claim 12, further comprising:
transmitting, with the computing system, the determined tilled floor profile of the field to a remote device.

17. The method of claim 13, further comprising:
geo-locating, with the computing system, the determined tilled floor profile of the field.

18. The method of claim 12, wherein the sensor frame corresponds to an unmanned aerial vehicle (UAV), the UAV including a body and a plurality of legs coupled to the body, the plurality of legs configured to support the body relative to the top surface of the field when the UAV is in a landed position at the data collection point.

19. The method of claim 12, wherein the sensor frame is configured to be moved relative to the field by an operator.

* * * * *